United States Patent [19]  [11] 4,189,612
Cohen et al.  [45] Feb. 19, 1980

[54] S-(+) 2,3,6-TRIMETHYL-5-(2,2,4-TRIMETHYL-1,3-DIOXOLANE-4-ETHYL)PHENOL

[75] Inventors: Noal Cohen, Montclair; Gabriel Saucy, Essex Fells, both of N.J.

[73] Assignee: Hoffmann-La Roche Inc., Nutley, N.J.

[21] Appl. No.: 7,278

[22] Filed: Jan. 29, 1979

Related U.S. Application Data

[62] Division of Ser. No. 895,424, Apr. 12, 1978, which is a division of Ser. No. 797,712, May 17, 1977, Pat. No. 4,113,740.

[51] Int. Cl.$^2$ ............................................... C07C 39/10
[52] U.S. Cl. ................................................. 568/763
[58] Field of Search .......................... 568/780, 763, 764

[56] References Cited

U.S. PATENT DOCUMENTS

| | | | |
|---|---|---|---|
| 3,415,844 | 12/1968 | Kulka | 568/763 |
| 4,113,740 | 9/1978 | Cohen | 568/764 |

Primary Examiner—Werren B. Lone
Attorney, Agent, or Firm—Jon S. Saxe; Bernard S. Leon; William H. Epstein

[57] ABSTRACT

Synthesis of optically active vitamin E from 2-methyl-5-oxotetrahydro-2-furoic acid including intermediates in this synthesis.

1 Claim, No Drawings

S-(+) 2,3,6-TRIMETHYL-5-(2,2,4-TRIMETHYL-1,3-DIOXOLANE-4-ETHYL)PHENOL

This is a division of application Ser. No. 895,424 filed Apr. 12, 1978, which in turn is a division application of Ser. No. 797,712 filed May 17, 1977 now U.S. Pat. No. 4,113,740.

BACKGROUND OF THE INVENTION

In the past, optically active alpha-tocopherol and derivatives thereof which are the 2R, 4'R, 8'R isomers of compounds of the formula:

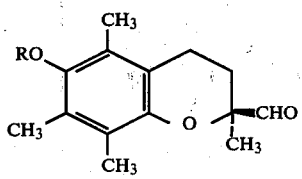

have been prepared through isolation from natural sources such as vegetable oil. This procedure suffers from many drawbacks due to the fact that the tocopherol content of these oils is very small. Therefore, a great amount of oil must be processed in order to isolate a small amount of natural tocopherol. Additionally, the process whereby various tocopherols are isolated from vegetable oil is extremely cumbersome.

SUMMARY OF INVENTION

In accordance with this invention, a process is provided for specifically synthesizing the 2(S)-isomer of the formula:

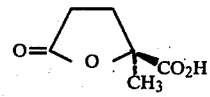

wherein R taken together with its attached oxygen atom forms an ester protecting group removable by hydrolysis or an ether protecting group removable by hydrogenolysis or acid catalyzed cleavage.

The compound of formula II can be converted to a compound of formula I via a Wittig reaction with a halide salt of the formula

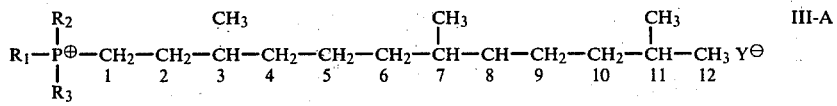

wherein $R_1$, $R_2$ and $R_3$ are aryl, where Y is halide ion.

The compound of the formula III can be a racemate or various 3 and 7 R and S isomers. Where the halide salt of formula III has a 3R,7R configuration, i.e.:

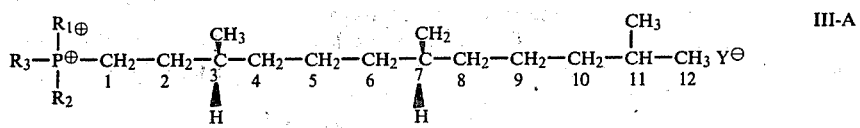

wherein $R_1$, $R_2$ and $R_3$ are as above then natural alpha-tocopherol is produced when the 2S isomer of the compound of formula II is utilized in the Wittig reaction.

The compound of formula II is produced in accordance with this reaction from a compound of the formula

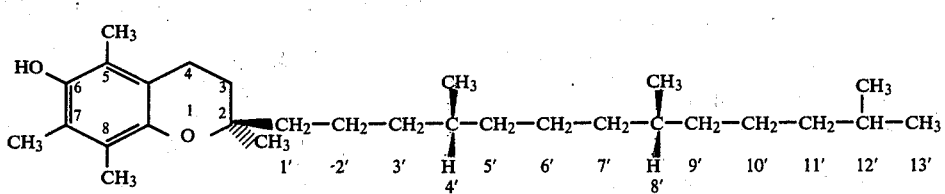

While only the formation of the 2(S) isomer of formula II is illustrated, the compound of formula II can be produced in any desired isomeric form depending upon the isomeric form of the compound of formula IV utilized as a starting material. If the 2R isomer of formula IV is utilized, then the 2R isomer of formula II will be produced. If a racemate of formula IV is utilized, than a racemate of formula II is formed. The reactions utilized in accordance with this invention maintain the same stereoconfiguration as in the compound of formula IV throughout its conversion to the compound of formula II.

DETAILED DESCRIPTION OF THE INVENTION

The numbering of the claims in formulas I, II, III and III-a, above, is shown for the purpose of convenience.

As used throughout this application, the term "lower alkyl" comprehends both straight and branched chain saturated hydrocarbon groups containing from 1 to 7 carbon atoms such as methyl, ethyl, propyl, isopropyl, etc. As used throughout this application, the term "halogen" includes all four halogens, such as bromine, chlorine, fluorine and iodine. The term "alkali metal" includes sodium, potassium, lithium, etc.

In the pictorial representation of the compounds given throughout this application, a ( ▼ ) tapered line indicates a substituent which is pointed out of the plane of the paper towards the reader and the (---) broken line indicates a substituent which is pointed into the plane of the paper away from the reader.

The term "lower alkoxy" as used throughout the specification denotes lower alkoxy groups containing from 1 to 7 carbon atoms such as methoxy, ethoxy, propoxy, isopropoxy, etc. The term "lower alkanoyl" as used throughout this specification denotes lower alkanoyl groups containing from 2 to 6 carbon atoms such as acetyl or propionyl. As used herein the term "aryl" designates mononuclear aromatic hydrocarbon groups such as phenyl, tolyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be unsubstituted or substituted with one or more of the aforementioned groups. The preferred aryl groups are the substituted and unsubstituted mononuclear aryl groups, particularly phenyl. The term "aryl lower alkyl" comprehends groups wherein aryl and lower alkyl are as defined above, particularly benzyl. The term "aroic acid" comprehends acids wherein the aryl group is defined as above. The preferred aroic acid is benzoic acid.

As still further used herein, the term "ester protecting group removable by hydrolysis" comprehends any conventional organic acid protecting group which can be removed by hydrolysis. Any conventional ester that can be hydrolyzed to yield the acid can be utilized as the protecting group. Exemplary esters useful for this purpose are the lower alkyl esters, particularly methyl, and the aryl esters particularly phenyl, and the aryl lower alkyl esters, particularly benzyl ester. The alcohols utilized to form the hydrolyzable ester protecting group are lower alkanols, aryl lower alkanols and reactive derivatives thereof.

The term "ether protecting group removable by hydrogenolysis or acid catalyzed cleavage" designates any ether which, upon acid catalyzed cleavage or hydrogenolysis yields the hydroxy group. A suitable ether protecting group is, for example, the tetrahydropyranyl ether or 4-methyl-5,6-dihydro-2H-pyranyl ether. Others are arylmethyl ethers such as benzyl, benzhydryl or trityl ethers or alpha-lower alkoxy lower alkyl ether, for example, methoxymethyl or allylic ethers, or trialkyl silyl ethers such as trimethyl silyl ether or dimethyl-tert.-butyl silyl ethers. Other ethers which are preferred are tertiary butyl ethers.

The preferred ethers which are removed by acid catalyzed cleavage are t-butyl and tetrahydropyranyl. Acid catalyzed cleavage is carried out by treatment with a strong organic or inorganic acid. Among the preferred inorganic acids are the mineral acids such as sulfuric acid, hydrohalic acid, etc. Among the preferred organic acids are lower alkanoic acids such as acetic acid, trifluoroacetic acid, etc. and arylsulfonic acids such as para-toluene sulfonic acid, etc. The acid catalyzed cleavage can be carried out in an aqueous medium or in an organic solvent medium. Where an organic acid is utilized, the organic acid can be the solvent medium. In the case of t-butyl, an organic acid is generally utilized with the acid forming the solvent medium. In the case of tetrahydropyranyl ethers, the cleavage is generally carried out in an aqueous medium. In carrying out this reaction, temperature and pressure are not critical and this reaction can be carried out at room temperature and atmospheric pressure.

The preferred ethers which are removable by hydrogenolysis are the aryl methyl ethers such as benzyl or substituted benzyl ethers. The hydrogenolysis can be carried out by hydrogenation in the presence of a suitable hydrogenation catalyst. Any conventional method of hydrogenation can be utilized in carrying out this procedure. Any conventional hydrogenation catalyst such as palladium or platinum can be utilized.

In accordance with this invention, the compound of formula VI is converted to the compound of formula II via the following intermediates:

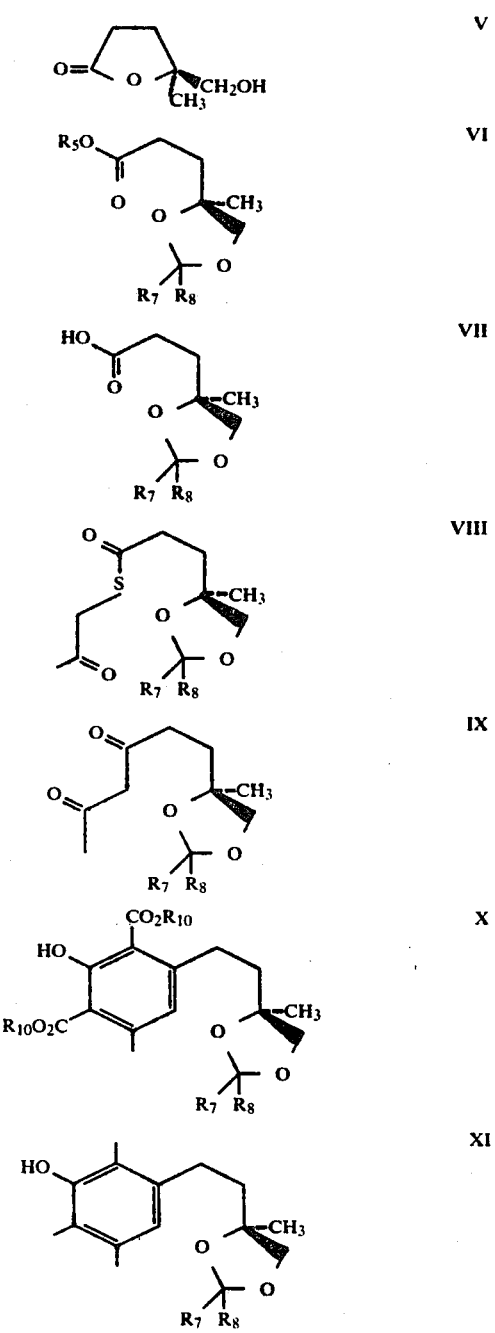

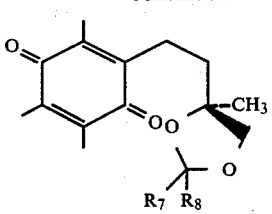 XII

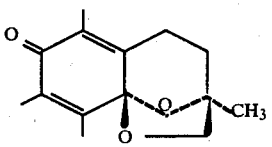 XIII

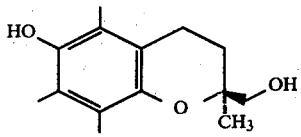 XIV

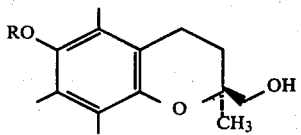 XV wherein R is as above; R$_5$, R$_7$, R$_8$, R$_{10}$ are lower alkyl.

The compound of formula IV is converted to the compound of formula V by selective reduction using a borane complex such as a borane-methyl sulfide complex in the manner described in Lane et al., J. Org. Chem 39, 3052 (1974). The compound of formula V is converted to the compound of formula VI by treating the compound of formula V with a compound of the formula

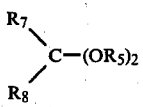 XVI wherein R$_5$, R$_7$ and R$_8$ are as above. The conversion of the compound of formula V to the compound VI utilizing the compound of formula XVI is carried out in the presence of a strong acid. Any conventional strong acid can be utilized in carrying out the process of this invention. Among the conventional acids are included the organic acids such as paratoluenesulfonic acid and the inorganic acids such as sulfuric acid and the hydrohalic acids such as hydrochloric acid. In carrying out this reaction, an inert solvent can be utilized. Among the preferred solvents are the organic solvents such as tetrahydrofuran, dioxane, etc. In carrying out this reaction, temperature and pressure are not critical and this reaction can be carried out at room temperature and atmospheric pressure. On the other hand, elevated temperatures can be utilized. Generally, temperatures of from 20° C. to 100° C. are utilized.

The compound of formula VI is converted to the compound of formula VII by saponification. Any conventional method of saponification can be utilized to affect this conversion. Among the preferred methods is by treating the compound of formula VI with a strong aqueous base and thereafter neutralizing the reaction medium. Any conventional alkali metal base such as sodium hydroxide or potassium hydroxide can be utilized. After treatment with the strong base, the resulting reaction mixture is neutralized by treatment with a aqueous inorganic acid such as sulfuric or hydrochloric acid. In carrying out this saponification reaction, temperature and pressure are not critical and the saponification reaction can be carried out at room temperature and atmospheric pressure. On the other hand, elevated temperatures and pressures can be utilized.

The conversion of the compound of formula VII to a compound of formula VIII is carried out by first treating the compound of formula VII with N,N'-carbonyldiimidazole followed by treatment with 2,5-dihydroxy-2,5-dimethyl-1,4-dithiane. This reaction can be carried out in an inert organic solvent medium. Any conventional inert organic solvent medium can be utilized to carry out this reaction. Among the preferred solvents are the ether solvents such as tetrahydrofuran, dioxane, diethyl ether, etc. The preferred solvent for use in this reaction is tetrahydrofuran. In carrying out this reaction, temperature and pressure are not critical and this reaction can be carried out at room temperature and atmospheric pressure. On the other hand, elevated or reduced temperatures can be utilized. Generally, this reaction is carried out at a temperature of from 0° C. to 100° C. with a temperature of from 20° C. to 40° C. being preferred. In carrying out this reaction, the carbonyldiimidazole is first added. The 2,5-dihydroxy-2,5-dimethyl-1,4-dithiane can be added shortly after or as soon as the addition of the carbonyldiimidazole is completed. In this reaction, an intermediate is formed after the addition of the carbonyldiimidazole. This intermediate has the formula:

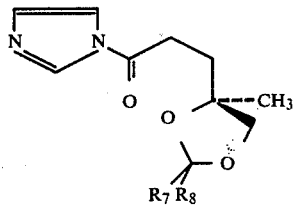 VII-A wherein R$_7$ and R$_8$ are as above.

The compound of formula VII-A is converted immediately upon reaction with 2,5-dihydroxy-2,5-dimethyl-1,4-dithiane to the compound of formula VIII. This reaction is carried out under the same conditions utilized to form the compound of formula VII-A. For instance, this reaction is carried out in an inert organic solvent medium. Any conventional inert organic solvent can be used as the reaction medium. Among the preferred solvents are the ether solvents such as tetrahydrofuran. As in the reaction with the dithiane, temperature and pressure are not critical and this reaction can be carried out at room temperature and atmospheric pressure. If desired, higher or lower temperatures can be utilized as described hereinbefore.

The compound of formula VIII is converted to the compound of formula IX by treatment with a bis [tertiary amino] alkyl or arylphosphine. Any conventional bis [tertiary amino], alkyl or aryl phosphine can be utilized. Among the preferred phosphines for use in this reaction is bis [3-dimethyl-amino-1-propyl] phenyl phosphine. The amino group in the phosphine is a tertiary amino group which is tri-substituted with lower alkyl moieties. The phosphorous substituent in the phosphine is also mono-substituted with either a lower alkyl or aryl substituent. Generally, this reaction is carried out in the presence of a lithium salt. Any conventional lithium salt such as a lithium halide can be utilized. Among the preferred lithium salts are lithium bromide, lithium chloride, etc. In carrying out this reaction, an inert organic solvent medium is utilized. Any conventional inert organic solvent such as acetonitrile, dimethyl formamide, tetrahydrofuran, dimethyl sulfoxide, etc. In carrying out this reaction, temperatures of from 50° C. to 120° C. are generally utilized, with temperatures of from about 80° to 100° C. being preferred.

The compound of formula IX is converted to the compound of formula X by reaction with a compound of the formula

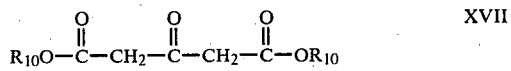

wherein $R_{10}$ is lower alkyl. This reaction is carried out in the presence of a strong base. Any conventional strong base can be utilized. Among the preferred strong bases are the alkali metal lower alkoxides such as sodium methoxide, potassium ethoxide, etc. Generally, this reaction is carried out in an inert organic solvent. Among the preferred solvents for carrying out this reaction are the lower alkanols such as methanol, ethanol, isopropanol, etc. In carrying out this reaction, temperature and pressure are not critical and this reaction can be carried out at room temperature and atmospheric pressure. On the other hand, higher or lower temperatures can be utilized. Generally, any temperature of from 10° C. to 125° C. can be utilized, with temperatures of from about 15° C. to 35° C. being preferred.

The compound of formula X is converted to the compound of formula XI by treating the compound of formula X with an aluminum hydride reducing agent at a temperature of from 120° C. to 180° C. In carrying out this reaction, any conventional aluminum hydride reducing agent which does not decompose at temperatures above 120° C., preferably from 120° C. to 180° C., can be utilized to carry out this reaction. Among the preferred aluminum hydride reducing agents are sodium dihydro-bis [2-methoxyethoxy] aluminate and di(lower alkyl) aluminum hydrides such as diisobutyl aluminum hydride. In carrying out this reaction, any inert organic solvent can be utilized. Among the preferred inert organic solvents are the inert organic solvents boiling above 120° C. at atmospheric pressure such as diglyme, xylene, etc. If desired, inert organic solvents which are lower boiling can be utilized. However, if these low boiling inert organic solvents are utilized, the reaction is carried out under pressure to prevent the solvent from boiling.

In accordance with another embodiment of this invention, the compound of formula X can be converted to the compound of formula XI via the following intermediates:

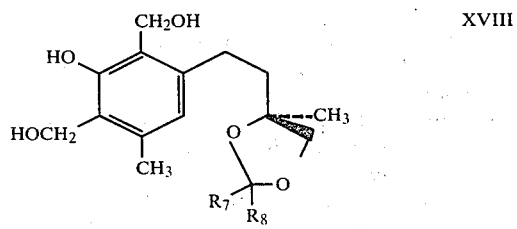

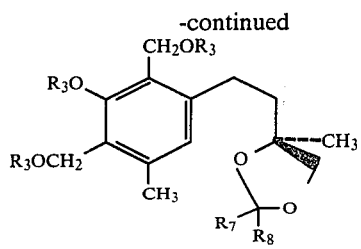

wherein $R_7$ and $R_8$ are as above and $R_3$ is a lower alkanoyl.

The compound of formula X is converted to the compound of formula XVIII by treating the compound of formula X with an aluminum hydride reducing agent at a temperature of from 0° to 100° C., preferably from 10° to 45° C. In carrying out this reaction, any conventional aluminum hydride reducing agent can be utilized. Among the preferred aluminum hydride reducing agents are included sodium aluminum hydride, diisobutyl aluminum hydride, sodium bis[2-methoxyethoxy] aluminum hydride. In carrying out this reaction, any conventional inert organic solvent can be utilized. Among the preferred solvents for use in this invention include tetrahydrofuran, dioxane, diethyl ether, benzene, toluene, xylene, etc.

The compound of formula XVIII is converted to the compound of formula XIX by treating the compound of formula XVIII with a lower alkanoic acid or a reactive derivative thereof. Among the reactive derivatives are included anhydrides of lower alkanoic acids, halides of lower alkanoic acids, etc. Any conventional method for reacting an alcohol with a lower alkanoic acid or a reactive derivative thereof to form an ester can be utilized to carry out this procedure. Among the preferred lower alkanoic acids are the alkanoic acids containing from 2 to 7 carbon atoms with acetic acid or acetic anhydride being the preferred reagent for reacting with the compound of formula XVIII.

The compound of formula XIX is converted to the compound of formula XI by treatment with an alkali metal boroydride reducing agent. Any of the conventional alkali metal borohydride reducing aents such as sodium borohydride can be utilized for this purpose. In carrying out this reaction, an inert organic solvent can be utilized. Among the preferred inert organic solvents are included dimethyl sulfoxide, dimethyl formamide, etc. In carrying out this reaction, temperatures of from 80° C. to 125° C. are utilized.

The compound of formula XI is converted to the compound of compound XII by oxidation with a nitroso sulfonate salt of the formula:

$$O-N(SO_3)_2Xm \qquad XXI$$

wherein X is an ammonium, alkali metal or alkaline earth metal ion, m is an integer of from 1 to 2 with the proviso that when X is an ammonium ion or a monovalent metal, m is 2 and when X is a divalent metal, m is 1.

Among the preferred nitroso sulfonate salts are included Fremy's salt. In carrying out this reaction, any of the conditions conventional in oxidizing with Fremy's salt as well as other nitroso sulfonate salts can be utilized. Generally, this reaction is carried out in an aqueous medium. In carrying out this oxidation, temperature and pressure are not critical and this reaction can be carried out at room temperature and atmospheric pressure. On the other hand, temperatures of from 0° C. to 30° C. can be utilized.

The compound of formula XII can be converted to the compound of formula XIII by treating the compound of formula XII with a strong acid in the presence of water. In carrying out this reaction, any conventional strong acid can be utilized. Among the preferred strong acids are included the inorganic acids such as sulfuric acid and hydrohalic acids, which include hydrobromic, hydrochloric, perchloric, etc. On the other hand, this reaction can be carried out utilizing strong organic acids such as the sulfonic acids. Among the strong organic acids are included methane sulfonic acid and paratoluene sulfonic acid. Generally, this reaction is carried out in an aqueous medium. On the other hand, if desired, an inert organic solvent can be utilized in combination with water as the reaction medium. The preferred inert organic solvents are the polar solvents. Any conventional polar solvent can be utilized in carrying out this reaction. Among the conventional inert organic polar solvents which can be utilized in the reaction medium are included tetrahydrofuran, acetonitrile, ethanol, etc. In carrying out this reaction, temperature and pressure are not critical and this reaction can be carried out at room temperature and atmospheric pressure. On the other hand, elevated or reduced pressures and temperatures can be utilized.

In accordance with another embodiment of this invention, the compound of formula XIII can be prepared from a compound of the formula XI via the following intermediates:

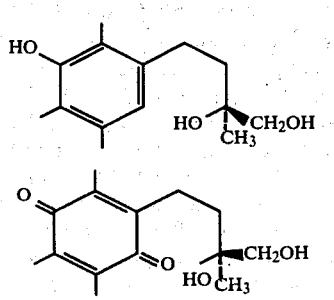

The compound of formula XI is converted to the compound of formula XXII by acid hydrolysis. Any conventional method of acid hydrolysis can be utilized to convert the compound of formula XI to the compound of formula XXII. The compound of formula XXII is converted to the compound of formula XXIII via oxidation with a nitroso disulfonate of the formula XXI. This oxidation is carried on in the same manner as disclosed with regard to the oxidation of a compound of the formula XI to a compound of the formula XII. The compound of formula XXIII is converted to a compound of formula XIII by treatment with a strong inorganic or organic acid in the same manner as described in connection with the conversion of a compound of the formula XII to a compound of the formula XIII. However, whereas the acid treatment of the compound of formula XII is carried out in the presence of water, the acid treatment of a compound of the formula XXIII to a compound of the formula XIII can be carried out in an anhydrous medium as well as in the presence of water. In the anhydrous medium, any inert organic solvent can be utilized. Among the preferred inert organic solvents are the solvents mentioned in connection with the conversion of the compound of formula XII to a compound of formula XIII.

The compound of formula XIII can be converted to a compound of formula XIV by treating the compound of formula XIII with a reducing agent or by catalytic hydrogenation. Among the preferred reducing agents are the hydride reducing agents such as disclosed hereinbefore. Any conventional hydride reducing agent such as the aluminum hydride reducing agents and the borohydride reducing agents can be utilized. Among the preferred hydride reducing agents are lithium aluminum hydride, sodium bis[2-methoxyethoxy]aluminum hydride as well as the borohydride reducing agents such as sodium borohydride can be utilized. In carrying out this reaction, any conventional inert organic solvent such as the solvents mentioned hereinbefore can be utilized as the reaction medium. Where catalytic hydrogenation is utilized, any conventional method of catalytic hydrogenation can be employed. Among the conventional hydrogenation catalysts, noble metals such as palladium and platinum including compounds thereof are generally preferred. In carrying out this conversion, temperature and pressure are not critical and room temperature and atmospheric pressure can be used. On the other hand, elevated or reduced temperatures and pressures can be utilized.

The compound of formula XIV is converted to the compound of formula XV by selective etherification to provide an ether protecting group, i.e. a phenolic ether protecting group removable by hydrogenolysis.

The compound of formula XV is converted to the compound of formula II by oxidation. Any conventional method of converting an alcohol to an aldehyde can be utilized to affect this reaction. Among the preferred oxidizing agents for use in this reaction are included silver carbonate, a chromium trioxide pyrridine complex [Collins reagent], chromium trioxide dispersed in a carrier such as graphite [Lalancette reagent] and chromium trioxide in pyridine [Sarett reagent]. In carrying out this oxidation, any of the conditions conventional in oxidizing with these reagents can be utilized.

In accordance with another embodiment of the invention, the compound of formula XXIII can be converted to the compound of formula XIV via the following intermediate

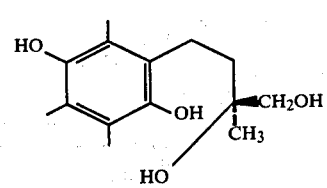

The compound of formula XXIII is converted to the compound of formula XXV by hydrogenation. Any conventional method of hydrogenation can be utilized to carry out this conversion. The hydrogenation can be carried out by hydrogenation utilizing conventional hydrogenation catalysts such as palladium or platinum. The compound of formula XXV is converted to the compound of formula XIV by treatment with a strong acid such as described in connection with the conversion of a compound of the formula XXII to a compound of the formula XIII.

In accordance with another embodiment of this invention, the compound of the formula XII can be converted to the compound of formula XIV via the following intermediate:

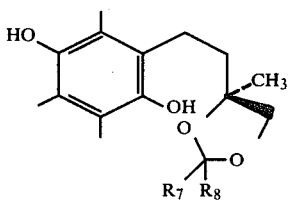

XXVI

The compound of formula XII is converted to the compound of formula XXVI by hydrogenation in the same manner as described in connection with the conversion of the compound of the formula XXIII to a compound of the formula XXV. The compound of the formula XXVI is converted to a compound of the formula XIV by treating the compound of the formula XIV with a strong acid in the presence of water. Any of the acids set forth in connection with the conversion of a compound of the formula XII to a compound of the formula XIII can be utilized in affecting this conversion. This acid treatment is carried out at temperatures of from 60° C. to 100° C. In the aqueous medium, there may be present, if desired, any conventional inert organic solvent. Any of the solvents mentioned hereinbefore in connection with the conversion of a compound of formula XII to a compound of formula XIII can be utilized in this conversion.

The following Examples are illustrative but not limitative of the invention. All temperatures are in degrees centigrade. The ether is diethylether in these Examples. The "usual work-up" involves three extractions with the specified solvent. Organic solutions were then washed with saturated brine, dried over anhydrous MgSO4, filtered and concentrated on a rotary evaporator, under water aspirator pressure. Residues were dried to constant weight under high vacuum at 40°–50° or water aspirator pressure in the case of volatile materials.

EXAMPLE 1

(S)-(+)-5-(hydroxymethyl)-5-methyldihydro-2(3H)-furanone

To a solution of 14.8 g. (102.7 mmol) of (S)-(−)-2-methyl-5-oxotetrahydro-2-furoic acid mp 84°–87° C.; $[\alpha]^{25}D - 16.56°$ in 70 ml. of dry tetrahydrofuran (THF) was added 10.1 ml. (8.1 g.; 106.7 mmol) of borane-methyl sulphide complex, dropwise, with stirring over a 0.5 hr. period. Occasional ice-bath cooling was employed to maintain the internal temperature below 30°. After stirring at room temperature for 1.5 hr., the reaction mixture was cautiously decomposed by the dropwise addition of 6.2 ml. of H2O. The mixture was then concentrated under water aspirator pressure and the residue was taken up in ethyl acetate and filtered. The solids were washed thoroughly with ethyl acetate and filtered. The solids were washed thoroughly with ethyl acetate and the filtrate and washes were combined and concentrated in vacuo giving (S)-(+)-5-(hydroxymethyl)-5-methyldihydro-2(3H)-furanone as a colorless oil (13.6 g.) which was used without further purification.

A sample of (S)-(+)-(hydroxymethyl)-5-methyldihydro-2(3H)-furanone prepared in this way was chromatographed on 40 parts of silica gel. Elution with 1:1 parts by volume benzene-ethyl acetate and ethyl acetate yielded the pure lactone which was recrystallized from ether-ligroine giving (S)-(+)-5-(hydroxymethyl)-5-methyldihydro-2(3H)-furanone as a colorless solid, mp 44.5°–46.5°; $[\alpha]^{25}D + 17.76°$ (c 1, CHCl3).

EXAMPLE 2

(S)-(+)-2,2,4-trimethyl-1,3-dioxolane-4-propanoic acid

A solution of (S)-(+)-5-(hydroxymethyl)-5-methyldihydro-2(3H)-furanone (13.6 g.; 104.6 mmol) and 283 mg. (1.64 mmol) of p-toluenesulfonic acid monohydrate in 161 ml. of 2,2-dimethoxy-propane was stirred at room temperature for 3.75 days. Pyridine (0.26 ml.) was then added and the mixture concentrated under water aspirator pressure. The residual ester (S)-(+)-methyl 2,2,4-trimethyl-1,3-dioxolane-4-propanoate was dissolved in 180 ml. of MeOH containing 29.27 g. (444 mmol) of 85% by weight aqueous KOH. The resulting solution was stirred at room temperature for 4 hrs. then concentrated in vacuo. The syrupy residue was diluted with ice water and the solution was extracted with ether (the ether extract was discarded). The aqueous, alkaline solution was layered with ether and carefully acidified to pH 2.6 (pH meter) with 3 N HCl. Work up with ether in the usual manner gave 16.1 g. (83.3% overall based on the furoic acid in Example 1 of (S)-(+)-2,2,4-trimethyl-1,3-dioxolane-4-propanoic acid as an oil. This material was used without further purification.

Crude (S)-(+)-2,2,4-trimethyl-1,3-dioxolane-4-propanoic acid was evaporatively distilled giving pure (S)-(+)-2,2,4-trimethyl-1,3-dioxolane-4-propanoic acid as a colorless oil, bp 80°–90° (bath temperature) (0.15 mmHg); $[\alpha]^{25}D + 1.58°$ (c 2.02, CHCl3).

EXAMPLE 3

(S)-(+)-methyl 2,2,4-trimethyl-1,3-dioxolane-4-propanoate

A solution of 6.3 g. (48.5 mmol) of (S)-(+)-5-(hydroxymethyl)-5-methyldihydro-2(3H)-furanone and 133 mg. of p-toluenesulfonic acid monohydrate in 75 ml. of 2,2-dimethoxypropane was stirred and refluxed for 3.5 hr. then cooled in an ice bath, diluted with ether and washed with saturated aqueous NaHCO3 solution. The organic solution was processed in the usual manner giving 8.2 g. of a yellow oil. This material was chromatographed on 400 g. of silica gel. Elution with 9:1 parts by volume and 4:1 parts by volume benzene-ethyl acetate gave the ester (S)-(+)-methyl 2,2,4-trimethyl-1,3-dioxolane-4-propanoate which was evaporatively distilled yielding 4.6 g. (47%) of a colorless liquid, bp 90°–100° (bath temperature) (12 mmHg); $[\alpha]^{25}D + 1.74°$ (c 2, C6H6). An analytical specimen of (S)-(+)-methyl 2,2,4-trimethyl-1,3-dioxolane-4-propanoate was obtained by rechromatography and redistillation of a sample; $[\alpha]^{25}D + 2.97°$ (c 2, C6H6).

EXAMPLE 4

(S)-(+)-4-[3,5-dioxo-1-hexyl]-2,2,4-trimethyl-1,3-dioxolane

To a stirred solution of 10 g. (53.2 mmol) of (S)-(+)-2,2,4-trimethyl-1,3-dioxolane-4-propanoic acid in 100 ml. of anhydrous THF was cautiously added 9.04 g. (55.8 mmol) of N,N'-carbonyldiimidazole (gas evolution). The resulting solution was stirred for 1 hour at room temperature then treated with 4.78 g. (26.6 mmol) of 2,5-dihydroxy-2,5-dimethyl-1,4-dithiane. Stirring was continued for 4 hrs. at room temperature then the reaction mixture was diluted with water and worked up with ether in the usual manner. The orange, oily residue (14.3 g.) was chromatographed on silica gel (400 g.). Elution with 9:1 parts by volume and 4:1 parts by volume benzene-ethyl acetate yielded 11.1 g. (80.2%) of thiol ester (S)-3-(2,2,4-trimethyl-1,3-dioxolan-4-yl)propanoic acid 2-oxo-propyl-S-ester as a yellow oil.

To a solution of 10.6 g. (40 mmol) of this thiol ester in 32 ml. of dry CH$_3$CN was added 3.85 g. (44.4 mmol) of anhydrous LiBr. After solution had occurred, 33 g. (123 mmol) of bis(3-dimethyl-amino-1-propyl)phenylphosphine was added. Separation of a solid soon began as the mixture was stirred and heated at 85°–90° C. After heating for 4.5 hr., the reaction mixture was cooled and poured into ice-water. The aqueous phase was layered with ether and acidified to pH 3.3 (pH meter) by the dropwise addition of 3 N aqueous HCl. Work-up with ether in the usual manner gave 8.7 g. of crude product as a yellow oil. This material was chromatographed on 350 g. of silica gel. Elution with 4:1 and 2:1 parts by volume hexane-ether gave the (S)-(+)-4-(3,5-dioxo-1-hexyl)-2,2,4-trimethyl-1,3-dioxolane which was evaporatively distilled. There was obtained 6.57 g. (72%) of pure (S)-(+)-4-(3,5-dioxo-1-hexyl)-2,2,4-trimethyl-1,3-dioxolane as a pale-yellow oil, bp 95°–105° (bath temperature) (0.005 mmHg); $[\alpha]^{25}D + 8.54°$ (c, 2, CHCl$_3$).

Basification of the acidic aqueous solution followed by ether extraction allowed recovery of the excess phosphine reagent.

EXAMPLE 5

(S)-(+)-dimethyl -2-hydroxy-6-methyl-4-(2,2,4-trimethyl-1,3-dioxolane-4-ethyl)-1,3-benzenedicarboxylate A solution of 6.0 g. (26.3 mmol) of (S)-(+)-dioxo-1-hexyl)-2,2,4-trimethyl-1,3-dioxolane from the preceding example and 5.83 g. (33.4 mmol) of dimethyl 1,3-acetonedicarboxylate in 33.6 ml. of 0.85 M methanolic NaOMe was stirred at room temperature for 21 hrs. The resulting yellow solution was poured into ice-water, layered with ether and the pH was adjusted to 3 by the addition of 3 N aqueous HCl. Work-up with ether in the usual manner gave 10.9 g. of a yellow oil. This material was chromatographed on 350 g. of silica gel. Elution with 9:1 and 4:1 parts by volume benzene-ethyl acetate gave 8.82 g. (91.7%) of (S)-(+)-dimethyl 2-hydroxy-6-methyl-4-(2,2,4-trimethyl-1,3-dioxolane-4-ethyl)-1,3-benzenedicarboxylate as a yellow oil; $[\alpha]^{25}D + 5.44°$ (c, 2, CHCl$_3$); Gc analysis indicated a purity of 92.4%. An analytical specimen was obtained by careful rechromatography and evaporative distillation giving pure (S)-(+)-dimethyl 2-hydroxy-6-methyl-4-(2,2,4-trimethyl-1,3-dioxolane-4-ethyl)-1,3-benzenedicarboxylate as a viscous, pale yellow oil, bp 125°–130° (bath temperature) (0.003 mmHg); $[\alpha]^{25}D + 6.07°$ (c, 2, CHCl$_3$).

EXAMPLE 6

(S)-(+)-2-hydroxy-6-methyl-4-(2,2,4-trimethyl-1,3-dioxolane-4-ethyl)benzene-1,3-dimethanol triacetate To a solution of 6.35 g. (17.3 mmol) of (S)-(+)-dimethyl 2-hydroxy-6-methyl-4-(2,2,4-trimethyl-1,3-dioxolane-4-ethyl)-1,3-benzenedicarboxylate in 138 ml. of anhydrous ether was added, dropwise, with stirring, 29 ml. of 70% sodium bis(2-methoxyethoxy)aluminum hydride in benzene. The reaction mixture was stirred at room temperature for 4 hrs. then at reflux for 16.5 hrs. After cooling, the mixture was cautiously poured onto ice-water. The aqueous phase was adjusted to pH 3.5 by the dropwise addition of 3 N aqueous HCl. Work-up with ether in the usual manner gave 4.44 g. (82.8%) of (S)-(+)-2-hydroxy-6-methyl-4-(2,2,4-trimethyl-1,3-dioxolane-4-ethyl)benzene-1,3-dimethanol as a yellow oil. This material was dissolved in 14.2 ml. of dry pyridine containing 6.5 ml. of acetic anhydride and the solution was stirred for 4.5 hrs. at room temperature then treated with 200 ml. of H$_2$O. Exces solid NaHCO$_3$ was added, followed by ether and the mixture was stirred for 15 min. The ether layer was separated and the aqueous layer was extracted three more times with ether. The combined ether extracts were stirred with 100 ml. of H$_2$O while the pH of the aqueous phase was adjusted to 4 by the addition of 3 N aqueous HCl. Work-up in the usual manner (the ether extracts were additionally washed with NaHCO$_3$ solution) gave 6.25 g. of (S)-(+)-2-hydroxy-6-methyl-4-(2,2,4-trimethyl-1,3-dioxolane-4-ethyl)benzene-1,3-dimethanol triacetate as an oil which was used without further purification. An 0.5 g. sample of this material was chromatographed on 50 parts of silica gel. Elution with ether gave 0.33 g. of pure (S)-(+)-2-hydroxy-6-methyl-4-(2,2,4-trimethyl-1,3-dioxolane-4-ethyl)benezene-1,3-dimethanol triacetate as a viscous, colorless oil; $[\alpha]^{25}D + 5.49°$ (c 2, CHCl$_3$).

EXAMPLE 7

(S)-(+)-2,3,6-trimethyl-5-(2,2,4-trimethyl-1,3-dioxolane-4-ethyl)phenol

To a solution of 5.75 g. of the crude (S)-(+)-2-hydroxy-6-methyl-4-(2,2,4-trimethyl-1,3-dioxolane-4-ethyl)benzene-1,3-dimethanol triacetate in 140 ml. of anhydrous dimethyl sulfoxide was added 4.96 g. (130 mmol) of NaBH$_4$. The resulting mixture was stirred and heated at 90°–100° for 4 hrs. then cooled and treated with 29 ml. of 1 N NaOH. After stirring for 1 hr. at room temperature, the mixture was diluted with ice-water (500 ml.) and acidified to pH 3.8 with 3 N HCl. Work-up with ether in the usual manner (the extracts were additionally washed with H$_2$O and saturated NaHCO$_3$ solution) gave 3.14 g. of a pale yellow oil. This material was chromatographed on 150 g. of silica gel. Elution with 19:1 and 9:1 parts by volume benzene-ethyl acetate afforded 2.5 g. of pure (S)-(+)-2,3,6-trimethyl-5-(2,2,4-trimethyl-1,3-dioxolane-4-ethyl)-phenol as a colorless oil which crystallized, mp 53°–60.5°. A portion of this material was recrystallized from hexane giving a colorless solid, mp 60°–62°; $[\alpha]^{25}D + 5.00°$ (c 2.0, CHCl$_3$).

EXAMPLE 8

A solution of 1.02 g. (2.79 mmol) of (S)-(+)-dimethyl 2-hydroxy-6-methyl-4-(2,2,4-trimethyl-1,3-dioxolane-4-ethyl)-1,3-benzenedicarboxylate in 5 ml. of xylene was added, dropwise, over a 5 min. period, to a stirred solution of 6 ml. (21.7 mmol) of 70% NaAlH$_2$(OCH$_2$C-H$_2$OMe)$_2$ (in benzene) in 5 ml. of xylene. The resulting solution was stirred and refluxed for 3.75 hrs. then cooled to 10° at which point a solution of 1.16 ml. of conc. H$_2$SO$_4$ in 5 ml. of H$_2$O was cautiously added, dropwise. The resulting slurry was diluted with 23 ml. of MeOH and stirred and refluxed for 10 min. After cooling, the slurry was filtered and the granular solid was washed with MeOH and then ether. The filtrate and washes were combined and concentrated in vacuo. The residue was taken up in ether and the solution was washed with brine and processed in the usual manner to give 769 mg. of a yellow oil. This material was chromatographed on 30 g. of silica gel. Elution with 4:1, 2:1 and 1:1 (parts by volume) hexane-ether afforded 640 mg. (82.5%) of (S)-(+)-2,3,6-trimethyl-5-(2,2,4-trimethyl-1,3-dioxolane-4-ethyl)phenol as a colorless oil which crystallized.

EXAMPLE 9

(S)-(+)-2,3,6-trimethyl-5-(2,2,4-trimethyl-1,3-dioxolane-4-ethyl)-p-benzoquinone A solution of 2.02 g. (7.66 mmol) of (S)-(+)-2,3,6-trimethyl-5-(2,2,4-trimethyl-1,3-dioxolane-4-ethyl)-phenol in 81 ml. of MeOH was added to a solution prepared from 65 g. (excess) of a slurry of disodium nitrosodisulfonate (Fremy's salt) in aqueous $Na_2CO_3$, 16 ml. of 1 N aqueous NaOAc and 484 ml. of $H_2O$. The brown mixture was stirred at room temperature for 1.5 hrs. then worked-up with ether in the usual manner. There was obtained 2.07 g. (97.6%) of essentially pure (S)-(+)-2,3,6-trimethyl-5-(2,2,4-trimethyl-1,3-dioxolane-4-ethyl)-p-benzoquinone as a viscous orange oil which was used without further purification. A sample was chromatographed on silica gel (50 parts). Elution with 4:1 parts by volume hexane-ether afforded an analytical specimen of (S)-(+)-2,3,6-trimethyl-5-(2,2,4-trimethyl-1,3-dioxolane-4-ethyl)-p-benzoquinone as a viscous orange oil, $[\alpha]^{25}D + 6.39°$ (c 2, $CHCl_3$).

EXAMPLE 10

(S)-(+)-5-(3,4-dihydroxy-3-methyl-1-butyl)-2,3,6-trimethylphenol

A solution of 1.4 g. (5.04 mmol) of (S)-(+)-2,3,6-trimethyl-5-(2,2,4-trimethyl-1,3-dioxolane-4-ethyl)-phenol in 28 ml. of MeOH and 5.5 ml. of 1 N aqueous HCl was stirred at room temperature for 20 hrs. then poured into saturated brine and worked-up with ether in the usual manner. Trituration of the solid residue with ether afforded 0.8 g. (66.7%) of pure (S)-(+)-5-(3,4-dihydroxy-3-methyl-1-butyl)-2,3,6-trimethylphenol as a colorless solid, mp 145°–146°; $[\alpha]^{25}D + 2.20°$ (c 2, EtOH).

The ether filtrate from the above trituration was concentrated and the residue was recrystallized from ethyl acetate giving an additional 139 mg. (11.7%) of (S)-(+)-5-(3,4-dihydroxy-3-methyl-1-butyl)-2,3,6-trimethylphenol.

EXAMPLE 11

(S)-(+)-5-(3,4-dihydroxy-3-methyl-1-butyl)-2,3,6-trimethyl-p-benzoquinone

An 0.5 g. (2.1 mmol) sample of (S)-(+)-5-(3,4-dihydroxy-3-methyl-1-butyl)-2,3,6-trimethyl-phenol was treated with Fremy's salt as in Example 9. There was obtained 480 mg. (90.7%) of (S)-(+)-5-(3,4-dihydroxy-3-methyl-1-butyl)-2,3,6-trimethyl-p-benzoquinone as a yellow solid, mp 109°–112.5°. Recrystallization from $CHCl_3$-hexane gave 370 mg. of yellow solid, mp 111.5°–113°; $[\alpha]^{25}D + 6.28°$ (c 2, $CHCl_3$).

EXAMPLE 12

(3S,9aR)-(−)-2,3,4,5,7,9a-hexahydro-3,6,8,9-tetramethyl-3,9a-epoxy-1-benzoxepin-7-one A solution of 1.5 g. (5.13 mmol) of (S)-(+)-2,3,6-trimethyl-5-(2,2,4-trimethyl-1,3-dioxolane-4-ethyl)-p-benzoquinone in 42 ml. of MeOH containing 8.3 ml. of 1 N aqueous HCl was stirred at room temperature for 18 hrs. then poured into saturated brine and worked-up with ether in the usual manner (the ether extracts were additionally washed with saturated aqueous $NaHCO_3$). The yellow solid product obtained (1.27 g.) was chromatographed on silica gel (100 g.) to remove a small amount of (S)-(+)-5-(3,4-dihydroxy-3-methyl-1-butyl)-2,3,6-trimethyl-p-benzoquinone. Elution with 19:1 and 9:1 (parts by volume) benzene-ethyl acetate yielded 870 mg. (72.5%) of (3S,9aR)-(−)-2,3,4,5,7,9a-hexahydro-3,6,8,9-tetramethyl-3,9a-epoxy-1-benzoxepin-7-one as a colorless solid, mp 99°–100° C.; $[\alpha]^{25}D - 56.04°$ (c 2, $C_6H_6$).

EXAMPLE 13

An 0.2 g. (0.8 mmol) sample of (S)-(+)-5-(3,4-dihydroxy-1-butyl)-2,3,6-trimethyl-p-benzoquinone was treated as in Example 12. The crude product (219 mg.) was chromatographed as above giving 157 mg. (84.8%) of pure (3S,9aR)-(−)-2,3,4,5,7,9a-hexahydro-3,6,8,9-tetramethyl-3,9a-epoxy-1-benzoxepin-7-one as a colorless solid, mp 96°–100°; $[\alpha]^{25}D - 54.29°$ (c 2.2, $C_6H_6$).

EXAMPLE 14

(S)-(+)-6-hydroxy-2,5,7,8-tetramethylchroman-2-methanol

To a stirred solution of 787 mg. (3.36 mmol) of (3S,9aR)-(−)-2,3,4,5,7,9a-hexahydro-3,6,8,9-tetramethyl-3,9a-epoxy-1-benzoxepin-7-one in 8.5 ml. of dry THF, at 0° C., was added 0.94 ml. (6.72 mmol) of 70% by weight $NaAlH_2(OCH_2CH_2OMe)_2$ solution in benzene, dropwise. The reaction mixture was stirred at 0° for 1 hr., then poured onto a mixture of ice and 1 N aqueous HCl. Work-up in the usual manner with ether afforded 717 mg. of solid product which was chromatographed on 50 g. of silica gel. Elution with 9:1, 4:1 and 2:1 parts by volume benzene-ethyl acetate yielded 647 mg. (81.6%) of pure (S)-(+)-6-hydroxy-2,5,7,8-tetramethylchroman-2-methanol as a colorless solid, mp 127°–129°; $[\alpha]^{25}D + 1.44°$ (c 2, EtOH).

EXAMPLE 15

A mixture of 200 mg. (0.834 mmol) of (3S,9aR)-(−)-2,3,4,5,7,9a-hexahydro-3,6,8,9-tetramethyl-3,9a-epoxy-1-benzoxepin-7-one and 223 mg. of powdered zinc in 10 ml. of glacial acetic acid was stirred at room temperature for 47 hrs. The mixture was then diluted with water, neutralized with $NaHCO_3$ and worked-up with ether in the usual manner. The crude, oily product (212 mg.) was chromatographed on 20 g. of silica gel. Elution with 19:1 and 9:1 (parts by volume) benzene-ethyl acetate gave 140 mg. (70%) of recovered (3S,9aR)-(−)-2,3,4,5,7,9a-hexahydro-3,6,8,9-tetramethyl-3,9a-epoxy-1-benzoxepin-7-one, mp 97°–99.5°. Further elution with 4:1 and 2:1 benzene-ethyl acetate afforded 60 mg. (30%) of (S)-(+)-6-hydroxy-2,5,7,8-tetramethylchroman-2-methanol as a colorless solid, mp 123°–127°.

EXAMPLE 16

A mixture of 200 mg. (0.834 mmol) of (3S,9aR)-(−)-2,3,4,5,7,9a-hexahydro-3,6,8,9-tetramethyl-3,9a-epoxy-1-benzoxepin-7-one, 200 mg. of 5% by weight palladium on 95% by weight charcoal and 50 ml. of ethanol was stirred in an atmosphere of hydrogen until gas uptake ceased (30 ml. $H_2$ consumed). The catalyst was filtered and the filtrate was concentrated in vacuo. Chromatography of the crude product on 20 g. of silica gel gave 150 mg. (76.2%) of (S)-(+)-6-hydroxy-2,5,7,8-tetramethylchroman-2-methanol as a colorless solid, mp 119°–125° C. [eluted with 4:1 and 2:1 (parts by volume) benzene-ethyl acetate].

EXAMPLE 17

(S)-(−)-6-benzyloxy-2,5,7,8-tetramethylchroman-2-methanol

A mixture of 0.55 g. (2.33 mmol) of (S)-(+)-6-hydroxy-2,5,7,8-tetramethylchroman-2-methanol, 790 mg. (5.72 mmol) of anhydrous $K_2CO_3$, 0.68 ml. (748 mg; 5.93 mmol) of benzyl chloride (distilled from and stored over $K_2CO_3$) and 4.5 ml. of DMF was stirred for 22 hrs. at room temperature then poured into $H_2O$ and worked up with ether in the usual manner. There was obtained 0.89 g. of a yellow oily product which was chromatographed on silica gel (35 g.). Elution with 19:1 and 9:1 benzene-ethyl acetate gave 724 mg. (97.1%) of (S)-(−)-6-benzyloxy-2,5,7,8-tetramethylchroman-2-methanol as a colorless solid, mp 66°–69.5°; $[\alpha]^{25}D - 2.35°$ (c 1.2, $CHCl_3$).

EXAMPLE 18

(S)-(+)-6-benzyloxy-2,5,7,8-tetramethylchroman-2-carboxaldehyde

To a stirred mixture of 36 ml. of dry $CH_2Cl_2$, 2.8 ml. of dry pyridine and 1.46 g. (14.6 mmol) of $CrO_3$ was added a solution of 645 mg. (1.98 mmol) of (S)-(−)-6-benzyloxy-2,5,7,8-tetramethylchroman-2-methanol in 5 ml. of $CH_2Cl_2$. The dark mixture was stirred for 40 min. at room temperature then the organic solution was decanted and the dark residue was washed with ether and $CH_2Cl_2$. The combined organic solutions were diluted with ether, washed with 1 N NaOH, $H_2O$ and 1 N HCl and work-up was then completed in the usual manner. The yellow oily product (590 mg.) was chromatographed on 50 g. of silica gel. Elution with 19:1 (parts by volume) hexane-ether gave 492 mg. (76.7%) of pure (S)-(+)-6-benzyloxy-2,5,7,8-tetramethylchroman-2-carboxyaldehyde as an oil which crystallized yielding a colorless solid, mp 56°–58°; $[\alpha]^{25}D + 11.89°$ (c 5.2, $CHCl_3$).

EXAMPLE 19

(2R,4′R,8′R)-α-tocopheryl-acetate

A solution of 570 mg. (1.03 mmol) of (3R,7R)-hexahydrofarnesyltriphenylphosphonium bromide in 5.6 ml. of anhydrous dimethoxyethane was stirred at room temperature while 0.43 ml. (1.03 mmol) of 2.4 M n-butyllithium in hexane was added. The resulting red solution was stirred for 2 hrs. at room temperature then a solution of 153 mg. (0.472 mmol) of (S)-(+)-6-benzyloxy-2,5,7,8-tetramethylchroman-2-carboxaldehyde in 1.5 ml. of anhydrous DME was added and stirring was continued for 3 hrs. at 65°–70°. After cooling, the reaction mixture was poured onto cold, dilute $H_2SO_4$ and work-up with ether was carried out in the usual manner. The product (520 mg.) was a mixture of oil and solid which was triturated with hexane. The hexane solution was decanted and concentrated in vacuo affording 287 mg. of oily material which was chromatographed on 15 g. of silica gel. Elution with 19:1 (parts by volume) hexane-ether yielded 168 mg. (68.7%) of 1′,2′-dehydrotocopherol benzyl ether as a colorless oil. This material (165 mg; 0.318 mmol) in 15 ml. of ethyl acetate was stirred with 68 mg. of 5% palladium on carbon, in an atmosphere of $H_2$, until gas uptake ceased. The catalyst was filtered and the filtrate was concentrated in vacuo giving 120 mg. (88.2%) of (2R,4′R,8′R)-α-tocopherol as a colorless oil which was homogeneous on tlc analysis. The ir and nmr spectra of this material were identical with those of natural d-α-tocopherol.

A solution of 112 mg. (0.26 mmol) of this material in 0.75 ml. of dry pyridine and 0.59 ml. of acetic anhydride was stirred at room temperature for 17 hrs. then concentrated under high vacuum. The residue was taken up in hexane and the solution was washed with $H_2O$ and brine and processed in the usual manner. The oily product was chromatographed on 7 g. of silica gel. Elution with 9:1 parts by volume hexane-ether gave (2R,4′R,8′R)-α-tocopheryl acetate (105 mg.). Evaporative distillation yielded 90 mg. (73.7%) of colorless oil, bp 205° (bath temperature) (0.02 mmHg).

EXAMPLE 20

A solution of 0.405 g (1.6 mmoles) of (S)-(+)-5-(3,4-dihydroxy-3-methyl-1-butyl)-2,3,6-trimethyl-p-benzoquinone in 20 ml of ethyl acetate was stirred in an atmosphere of hydrogen, in the presence of 0.04 g of 5% by weight palladium on 95% by weight charcoal until $H_2$ uptake ceased (ca. 1 hr; 38 ml $H_2$ absorbed). The catalyst was filtered and the filtrate was concentrated giving 0.41 g of (S)-5-(3,4-dihydroxy-3-methyl-1-butyl)-2,3,6-trimethylhydroquinone as a tan solid, mp 124°–131.5°.

EXAMPLE 21

A mixture of 0.32 g (1.26 mmoles) of (S)-5-(3,4-dihydroxy-3-methyl-1-butyl)-2,3,6-trimethylhydroquinone, 25 mg of p-toluene sulfonic acid monohydrate and 25 ml of benzene was stirred and refluxed for 1.25 hr. The resulting solution was cooled, washed with $NaHCO_3$ solution and processed in the usual manner giving 0.393 g of a semi-solid residue which was chromatographed on 25 g of silica gel. Elution with 9:1, 4:1 and 2:1 (parts by volume) toluene-ethyl acetate yielded 0.237 g (79.7%) of (S)-(+)-6-hydroxy-2,5,7,8-tetramethylchroman-2-methanol as a cream-colored solid, mp 122°–124° C.; $[\alpha]_D + 1.09°$ (c 2.195, EtOH).

EXAMPLE 22

A 0.531 g (1.82 mmoles) sample of (S)-(+)-2,3,6-trimethyl-5-(2,2,4-trimethyl-1,3-dioxolane-4-ethyl)-p-benzoquinone was hydrogenated as described above in example 20. A total of 50 ml of $H_2$ was absorbed. There was obtained 0.54 g of (S)-2,3,6-trimethyl-5-(2,2,4-trimethyl-1,3-dioxolane-4-ethyl)hydroquinone as a tan solid.

EXAMPLE 23

A solution of 0.455 g (1.54 mmoles) of (S)-2,3,6-trimethyl-5-(2,2,4-trimethyl-1,3-dioxolane-4-ethyl)hydroquinone and 2 ml of 1 N aqueous sulfuric acid in 10 ml of methanol was stirred and refluxed for 1.5 hr. After cooling, the reaction mixture was treated with saturated brine and worked-up with ether in the usual manner giving 0.362 g of a brown glass. This material was triturated with ether giving a solid which was removed by filtration. The ether solution was chromatographed on 25 g of silica gel. Elution with 4:1 and 2:1 toluene-ethyl acetate afforded 0.125 g (34.4%) of (S)-(+)-6-hydroxy-2,5,7,8-tetramethylchroman-2-methanol as a colorless solid, mp 124.5°–127.5°; $[\alpha]_D^{25} + 1.04°$ (c 2.115, EtOH).

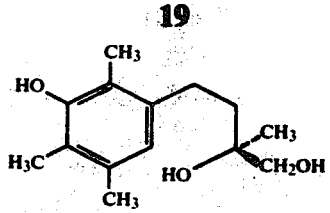

We claim:

1. A compound of the formula: